United States Patent [19]

Kovacic et al.

[11] Patent Number: 5,069,910
[45] Date of Patent: Dec. 3, 1991

[54] DISPERSIBLE CIMETIDINE TABLETS

[75] Inventors: Mateja Kovacic; Jenny Milovac, both of Ljubljana; Polona Cvelbar, Velike Lasce; Anton Stalc, Ljubljana; Zvezdana Trost, Vrhnika; Zdravko Kopitar, Menges; Bojan Kofler, Skofja Loka; Vida Nikolic, Ljubljana; Marija Lampret, Sentvid pri Sticni; Marija Lippai, Ljubljana, all of Yugoslavia

[73] Assignee: Lek, Yugoslavia

[21] Appl. No.: 366,437

[22] Filed: Jun. 15, 1989

[30] Foreign Application Priority Data

Jun. 23, 1988 [YU] Yugoslavia ................... 1209/88

[51] Int. Cl.$^5$ ................................. A61K 9/20
[52] U.S. Cl. ............................ 424/464; 424/465; 424/467; 424/468; 424/470; 424/456
[58] Field of Search ............... 424/464, 456, 468, 465, 424/467, 470

[56] References Cited

U.S. PATENT DOCUMENTS

| | | | |
|---|---|---|---|
| 4,693,895 | 9/1987 | Wong et al. | 424/469 |
| 4,764,380 | 8/1988 | Urguhart et al. | 424/468 |
| 4,824,664 | 4/1989 | Tarral et al. | 424/43 |
| 4,851,228 | 7/1989 | Zentner et al. | 424/456 |
| 4,853,229 | 8/1989 | Theeuwes | 424/455 |

OTHER PUBLICATIONS

A Lievermann, Pharmaceutical Dosage Forms: Tablets, vol. 1 (1980) 79–141.
The Merck Index, 10th Edition (1983), 7432.
H. P. Fieldler, Lexikon der Holfsstoffe fur Pharmazie, Kosmetik und Angrenzende Gebiete, pp. 1123–1125.

Primary Examiner—Thurman Page
Assistant Examiner—Louis A. Piccone
Attorney, Agent, or Firm—Pollock, Vande Sande & Priddy

[57] ABSTRACT

There are described novel dispersible cimetidine tablets containing 30 to 90% by weight of one of the polymorphous modifications of cimetidine A, B or C, 5 to 55% by weight of one or more disintegrationg agents, 0.05 to 5.0% by weight of a surfactant, such as sodium lauryl sulphate together with other common adjuvants. The process for the manufacture of dispersible cimetidine tablets is effected on the basis of known methods by granulating the ingredients and by compressing the granulate to tablets. Dispersible tablets disintegrate when brought in contact with water at room temperature within less than 1 minute to yield a fine dispersion, which facilitates the oral application. Therefore such tablets are particularly suitable for certain groups of patients, especially for the aged and children. Dispersible tablets containing cimetidine excell by their improved rate of dissolution and good bioavailability.

13 Claims, 1 Drawing Sheet

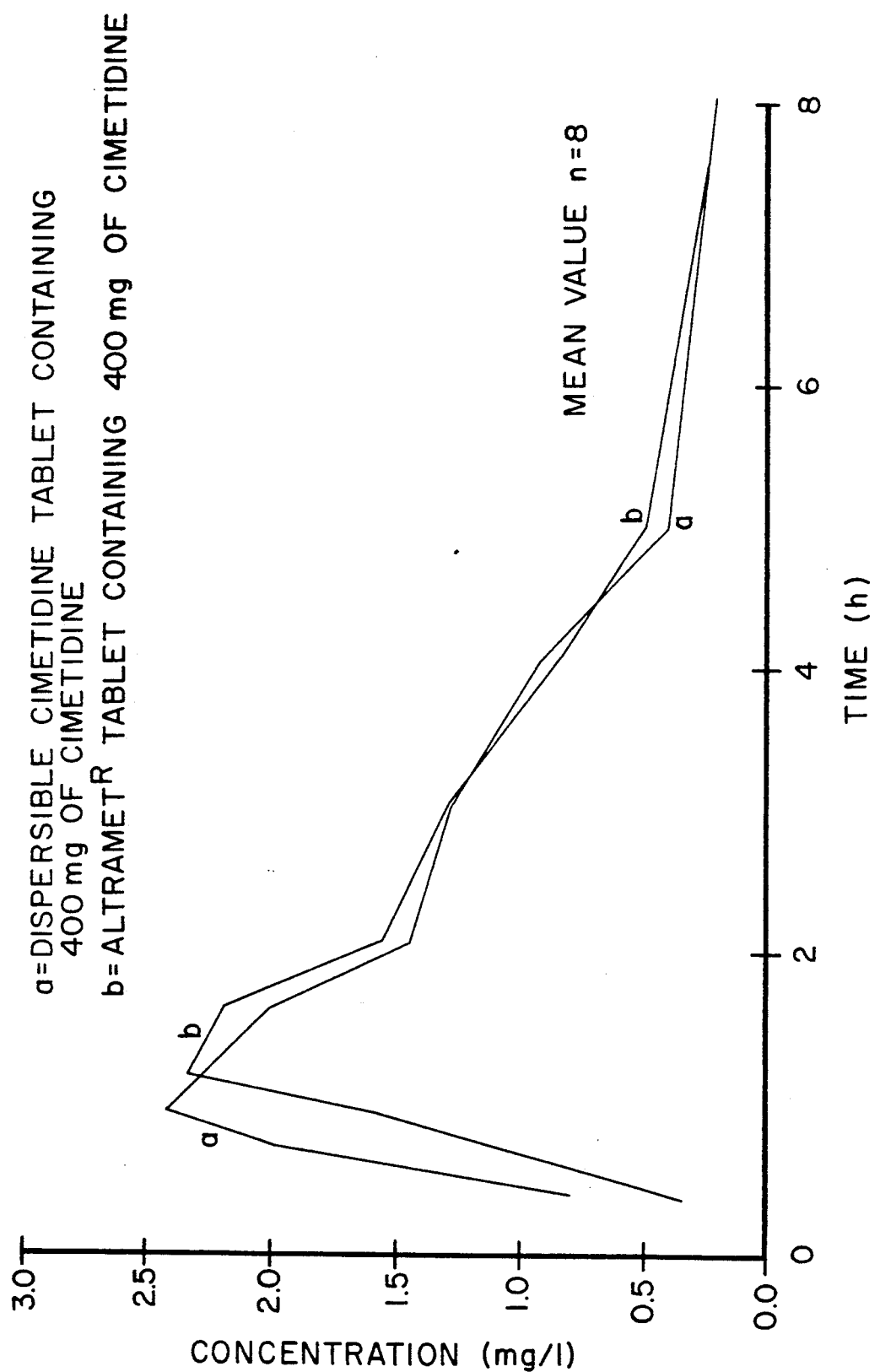

DISPERSIBLE CIMETIDINE TABLETS

TECHNICAL FIELD OF THE INVENTION (IPC A 61 K 31/635;A 61 K 9/20)

The invention belongs to the field of pharmaceutical industry and relates to dispersible tablets containing cimetidine, which yield a fine dispersion when brought in contact with water. Cimetidine is the generic name of 1-cyano-2-methyl-3-/2-//(5-methyl-4-imidazol-4-yl)methyl/thio/ethyl/guanidine, which is a well-known histamine antagonist on $H_2$ receptors and is a valuable drug in the therapy of ulcer disease. Cimetidine is known to occur in three polymorphous modifications designated as cimetidine A, B, and C. Dispersible cimetidine tablets of the invention can contain any one of said polymorphous modifications of cimetidine.

Furthermore, the invention relates to a process for the manufacture of dispersible cimetidine tablets. By formulating cimetidine into dispersible tablets a new pharmaceutical form is provided, which is, with respect to the mode of application, at the same dose preferred to the conventional tablet for oral administration in pediatrics and geriatrics.

TECHNICAL PROBLEM

There exists a constant need for novel stable galenic forms on the basis of cimetidine for the treatment of ulcer disease, which will possess improved biopharmaceutical properties and will be particularly suitable for certain groups of patients, especially for the aged and children. cl PRIOR ART At the treatment of the active phase of peptic ulcer with cimetidine, the daily dosage is in the range from 800 to 1200 mg, divided in two or four doses. According to some recent therapeutic findings, a single daily dose of 800 mg of cimetidine is also possible in the therapy of the active phase. In any case, comparatively large doses are involved, which cause trouble to many patients already at taking the medication in the form of too large tablets. This can be overcome by using effervescent or dispersible tablets. Effervescent tablets are based on the reaction of a bicarbonate or carbonate with an acid or on some other excipient having the ability of developing gas after being brought in contact with water; however, the technology of manufacturing effervescent tablets is expensive and demanding and it requires working at low relative humidity (below 30%). The manufacture of dispersible tablets is simpler and less expensive and can be carried out at normal relative humidity.

Dispersible tablets are based on the presence of disintegrating agents having the ability to swell with water. Dispersible tablets rapidly disintegrate in water at room temperature to form a milky solution. This form of administration is particularly suitable for certain groups of patients, especially for the aged and children.

From EP 138 540 there is known a viscous syrup containing cimetidine, which due to the presence of a buffering agent has a less bitter taste than unbuffered suspensions.

From the point of view of transport, storage and daily handling, however, the use of a ready-for-use syrup is rather demanding. Therefore dispersible tablets represent a preferred form in comparison with liquid oral preparations. By the use of dispersible tablets it is also possible to extend the period of applicability of the preparation.

GB-A-2 067 900 discloses the preparation of dispersible tablets containing trimethoprim and sulphamethoxazole as active ingredients and cross-linked polyvinylpyrrolidone as disintegrating agent. The tablets disintegrate within less than 1 minute. A 100% dissolution of trimethoprim in 0.1N hydrochloric acid is achieved within 15 minutes. EP-B-003 589 discloses another example of dispersible tablets containing an antacid ingredient, such as aluminium hydroxide and magnesium hydroxide, together with a disintegrating agent, preferably sodium starch glycolate having a swelling capacity between 5 and 100 ml/g.

EP-A-181 650 discloses dispersible tablets containing cyclandelate, which yield a fine dispersion after contact with water of 20° C.; the tablets consist of a rapidly dispersible core containing one or more active substances, which is covered by a coating, which is also rapidly dispersible. This form is particularly suitable for active ingredients that are prone to recrystallisation and/or sublimation.

BRIEF DESCRIPTION OF THE DRAWINGS

FIG. 1 represents a comparison of plasma concentration levels of cimetidene for a dispersible tablet containing 400 mg cimetidene and a dispersible tablet commercially available under the trademark Altramet also containing 400 mg of cimetidene.

DESCRIPTION OF THE SOLUTION OF THE TECHNICAL PROBLEM WITH EXAMPLES

The invention is based on the problem how to prepare novel, stable dispersible tablets containing cimetidine, which after contact with water at room temperature will disintegrate within less than 1 minute to yield a fine, flavoured dispersion suitable for oral administration. The dispersible tablets possess an improved rate of dissolution and good bioavalilability.

Dispersible tablets of the invention contain, as the active substance, 30 to 90% by weight of cimetidine having a particle size of less than 200 $\mu$m with 95% of particles having a size of between 20 and 100 $\mu$m.

The essential ingredients imparting the desired properties to the dispersible tablets and making possible a rapid swelling and/or good wettability of the tablets and thereby a quick disintegration thereof are disintegrating agents, such as corn or potato starch or modified starches (sodium carboxymethyl starch etc.), microcrystalline cellulose, alginic acid and derivatives thereof, formaldehyde case in products (e.g. Esma-Spreng ®), cross-linked sodium carboxymethyl cellulose (e.g. Ac-DiSol ®), cyclodextrin polymers and others. It has been found that the best disintegration is achieved with a combination of two or more disintegrating agents, which are contained in the tablet in an amount from 5 to 55% by weight.

The tablets can also contain other ingredients, which are known in pharmacy and used in the manufacture of tablets and dispersible tablets, such as binders, e.g. cellulose, polyvinylpyrrolidone, starch etc., lubricating agents, e.g. magnesium stearate, stearic acid, polyethylene glycols, talcum, silica (Aerosil 200 V ®) etc., fillers, e.g. mannitol or sorbitol, as well as flavouring and taste-improving substances, e.g. sodium saccharin, menthol etc.

It has been found that an improved rate of dissolution of cimetidine from dispersible tablets is achieved if they contain from 0.05 to 5.0% by weight, preferably from 0.1 to 0.2% by weight of a surfactant, such as sodium lauryl sulphate (Texapon K 12), various polysorbates known under the trade name Tween ®, ethers of polyhydroxy ethylene fatty acids known under the trade name Brij ®, esters of polyhydroxy ethylene fatty acids known under the trade name Myrj ®, sodium desoxycholate, glycerol polyethylene glycol ricinoleate (Cremophor EL ®), polyoxyethylene-polyoxypropylene polymers known under the trade name Pluronic ®, various polyalkoxy alkylene sterol ethers, wherein the sterol moiety is selected from the group consisting of lanosterol, dihydrocholesterol and cholesterol known under the trade names Solulan ® (e.g. Solulan ® C-24) of the formula $$RO(CH_2)_n-OH$$

wherein RO denotes the sterol moiety, such as lanosterol, dihydrocholesterol or cholesterol radical, n is an integer of 2 or 3 and x represents a number between 8 and 30. Preferred polyoxyalkylene ethers to be used according to the invention are polyoxyethylene or polyoxypropylene ethers (n=2 or 3) having a HBL value ("hydrophilic-lipophilic balance") from about 10 to about 20, particularly from about 12 to about 16 (cf. H. P. Fiedler, Lexikon der Hilfsstoffe für Pharmazie, Kosmetik and angrenzende Gebiete, 2nd Edition, 1981, Editio Cantor, Aulendorf, FRG). These surfactants improve the resorption of the active substance in the gastrointestinal tract.

The improved rate of dissolution of cimetidine from dispersible tablets containing added surfactant in comparison with dispersible tablets that do not contain this additive or with the common commercial preparation, i.e. coated tablets, is an important novelty.

Preferably, sodium lauryl sulphate is used as surfactant.

The process for the manufacture of dispersible cimetidine tablets comprises the steps of blending cimetidine, mannitol and an ethanolic solution of the surfactant to produce a moist granulate, which is passed through an oscillatory sieve, dried and again finely sieved. To the dry granulate there are added disintegrating agents, such as microcrystalline cellulose, potato or corn starch, modified starches etc. together with the rest of the adjuvants. The obtained mixture is passed through an oscillatory sieve and then tabletted to tablets of desired size and shape. The thus obtained dispersible tablets disintegrate after contact with water at room temperature within less than 1 minute to yield a fine dispersion suitable for therapeutical use. The content of cimetidine in the tablet can be 200 mg, 300 mg, 600 mg or 800 mg, preferably 400 mg. With respect to stability the dispersible tablets are comparable to the commercial cimetidine preparations (tablets) and therefore the same packing material (vials, blister-packs, strips) can be used.

The invention is illustrated by the following non-limitative Examples.

EXAMPLE 1

Dispersible Tablets Containing 400 mg of Cimetidine

| Ingredients | mg/tablet | % |
| --- | --- | --- |
| cimetidine | 400 | 47.6 |
| sodium lauryl sulphate (Texapon ® -K 12) | 1.0 | 0.120 |
| mannitol | 100.0 | 12.0 |
| starch (potato) | 70.0 | 8.33 |
| magnesium stearate | 5.0 | 0.595 |
| talcum | 40.0 | 4.76 |
| silica (Aerosil ® 200) | 4.0 | 0.476 |
| sodium saccharin | 10.0 | 1.20 |
| menthol | 6.0 | 0.714 |
| microcrystalline cellulose (Avicel ® 101) | 204.0 | 24.276 |

Method for the Manufacture of 10,000 Tablets 4 kg of cimetidine were blended with 1 kg of mannitol and moistened with an ethanolic solution containing 10 g of sodium lauryl sulphate dissolved in 1.2 kg of ethanol. The moist granulate was passed through an oscillatory sieve having 2.5 mm openings, dried and then again passed through a sieve with 0.75 mm openings. To the mixture there were added 2.040 kg of microcrystalline cellulose, 0.700 kg of potato starch, 0.400 kg of talcum, 0.050 kg of magnesium stearate, 0.040 kg of Aerosil ®, 0.1 kg of sodium saccharin and 0.060 kg of menthol.

Finally, the mixture was passed through an oscillatory sieve having 0.75 mm openings and tabletted on a rotatory tabletting machine.

Thus there were obtained oblong, crowned tablets weighing 840 mg, having a hardness of 49 to 78.4N and a friability of 0.5%. The hardness was tested in an Erweka TBH 28 hardness-tester, the friability in an Erweka TA friability-tester. After immersion in 250 ml of water, the tablet disintegrated in less than 1 minute, yielding a fine dispersion suitable for therapeutic application.

EXAMPLE 2

Dispersible Tablets Containing 400 mg of Cimetidine

The procedure of Example 1 was followed except that 2.0 mg (0.24%) of a polyoxyethylene-polyoxypropylene polymer (Pluronic ® F 68) were used instead of sodium lauryl sulphate.

EXAMPLE 3

Dispersible Tablets Containing 400 mg of Cimetidine

The procedure of Example 1 was followed except that 10.0 mg (1.2%) of polyalkoxy-alkylene sterol ether (Solulan ® 16), obtained by alkoxylation of 1 equivalent of lanolin alcohol with about 16 equivalents of ethylene oxide, were used instead of sodium lauryl sulphate.

EXAMPLE 4

Dispersible Tablets Containing 400 mg of Cimetidine

The procedure of Example 1 was followed except that 10.0 mg (1.2%) of polyalkoxyalkylene sterol ether (Solulan ® 24), obtained by the alkoxylation of 1 mole of cholesterol with about 24 moles of ethylene oxide, were used instead of sodium lauryl sulphate.

EXAMPLE 5

Dispersible Tablets Containing 800 mg of Cimetidine

| Ingredients | mg/tablet | % |
| --- | --- | --- |
| cimetidine | 800 | 47.60 |
| sodium lauryl sulphate (Texapon ® -K 12) | 3.0 | 0.17 |
| mannitol | 200.0 | 12.0 |
| starch (potato) | 140.0 | 8.30 |

-continued

| Ingredients | mg/tablet | % |
|---|---|---|
| magnesium stearate | 10.0 | 0.59 |
| talcum | 80.0 | 4.76 |
| silica (Aerosil ® 200) | 8.0 | 0.47 |
| sodium saccharin | 18.0 | 1.07 |
| menthol | 12.0 | 0.71 |
| microcrystalline cellulose (Avicel ® 101) | 409.0 | 24.33 |

The procedure of Example 1 was followed except that larger tablets weighing 1680 mg were manufactured, which after immersion in water at room temperature disintegrated in less than 1 minute, yielding a fine dispersion suitable for therapeutic application.

EXAMPLE 6

Dissolution Rates of Cimetidine from Dispersible Tablets and from a Commercial Preparation There were determined the disintegration rate of dispersible tablets containing 400 mg of cimetidine and the dissolution rates of cimetidine from dispersible tablets containing 400 mg cimetidine together with a surfactant and from dispersible tablets containing no such additive as well as the dissolution rate of cimetidine from the commercial preparation of cimetidine Altramet ® (Lek, Ljubljana) (tablets containing 400 mg of cimetidine).

Disintegration Rate, Release Rate of Cimetidine from Dispersible Tablets

The tablet was placed in a beaker containing 100 ml of water at a temperature of about 22° C. The tablet disintegrated within 30 to 60 seconds; after a thorough stirring there resulted a homogeneous suspension.

In this sample the quantity of the dissolved active substance was determined as shown in Table 1.

TABLE 1

The percentage of dissolved cimetidine in the test sample

| Dispersible tablet/100 ml water | % of dissolved cimetidine | | | |
|---|---|---|---|---|
| | 1 | 2 | 3 | 4 |
| tablet without added surfactant | 62.9 | 61.9 | 68.4 | 60.1 |
| tablet with added sodium lauryl sulphate | 83.2 | 81.2 | 84.9 | 89.4 |

The percentage of the dissolved active substance in the thus prepared test sample was greater for the tablets with added sodium lauryl sulphate. Consequently, the addition of a surfactant increases the quantity of dissolved cimetidine in water.

Dissolution Rate Test

Method A

The test was performed by Paddle Method on Apparatus 2 according to USP XXI for the dissolution rate determination. The speed of the paddle was 100 rpm, the dissolution medium was 250 ml of water at a temperature of 22°±1° C. The time of sampling was 1, 2 and 5 minutes after the start of the test.

Table 2 shows the time dependence of cimetidine dissolution from dispersible tablets containing a surfactant as additive and from dispersible tablets with no such additive in water at a temperature of 22°±1° C.

TABLE 2

| | % of dissolved cimetidine | | | | | | mean value |
|---|---|---|---|---|---|---|---|
| | 1 | 2 | 3 | 4 | 5 | 6 | ± S.D. |
| tablet with added sodium lauryl sulphate | | | | | | | |
| 1 min | 83.9 | 74.8 | 78.4 | 76.3 | 84.1 | 74.5 | 78.7 ± 3.3 |
| 2 min | 92.8 | 87.1 | 88.7 | 90.4 | 94.7 | 93.9 | 91.3 ± 3.1 |
| 5 min | 99.3 | 96.5 | 99.2 | 98.4 | 100.5 | 100.1 | 99.1 ± 1.4 |
| tablet without added sodium lauryl sulphate | | | | | | | |
| 1 min | 69.6 | 61.2 | 65.3 | 62.9 | 61.4 | 69.3 | 65.0 ± 3.8 |
| 2 min | 70.6 | 76.8 | 77.8 | 76.5 | 73.6 | 77.1 | 75.4 ± 2.8 |
| 5 min | 81.1 | 87.6 | 88.1 | 87.3 | 84.5 | 87.0 | 85.9 ± 2.7 |

Table 2 shows the characteristics of cimetidine dissolution in water at the temperature of 22° C. The test results show that the dissolution rate of cimetidine from a dispersible cimetidine tablet with added surfactant is greater than from a tablet without added surfactant, the percentage of the dissolved active substance in the homogeneous suspension being over 75% after 1 min and over 90% after 2 min.

Method B

The test was performed on Apparatus 1 according to USP XXI for the determination of dissolution rates. The speed of the basket was 100 rpm, the dissolution medium were 900 ml of water at a temperature of 37°±0.5° C. The dissolution rates of cimetidine from dispersible tablets with added surfactant and from a commercial preparation of cimetidine (coated tablets containing 400 mg of cimetidine, Altramet ®, Lek Ljubljana) in in vitro conditions were compared. The results are shown in Table 3.

TABLE 3

| | % of dissolved cimetidine[a] after | | | |
|---|---|---|---|---|
| | 2 min | 5 min | 10 min | 15 min |
| commercial preparation Altramet ® tablets containing 400 mg of cimetidine | 60.2 | 84.6 | 91.9 | 94.9 |
| dispersible cimetidine tablets containing 400 mg of the active substance | 90.5 | 99.1 | | |

[a]The results represent the mean value of tests on six tablets.

USP XXI U.S. Convention (1985), 1243 to 1244 requires that at least 75% of cimetidine should dissolve within 15 minutes. From comparative tests of both preparations and from Table 3 it can be seen that dispersible cimetidine tablets according to the present invention dissolve practically quantitatively already within 5 minutes.

Comparison of Bioavailability of Cimetidine after P.O. Administration of the Dispersible Tablet and of the Commercial Preparation The dispersible cimetidine tablets were tested in vivo in comparison with a commercial preparation (Altramet ® tablets, Lek Ljubljana). Both preparations were administered to 8 healthy male persons. Blood samples were taken from each person 0, 15, 30 and 45 minutes and 1, 1.5, 2, 3, 4, 5, and 8 hours after the administration. Blood plasma was quickly separated and kept at −20° C. up to the analysis of the plasma concentration of cimetidine by HPLC ("high performance liquid chromatography") method.

The results are shown in Table 4 and in Graph I.

TABLE 4

|  | dispersible tablet containing 400 mg of cimetidine | commercial preparation containing 400 mg of cimetidine |
|---|---|---|
| AUC | 8.21 ± 0.47 (mg.h/l) | 7.96 ± 2.67 (mg.h/l) |
| $C_{max}$ | 2.55 ± 0.20 (mg/l) | 2.44 ± 0.59 (mg/l) |
| $t_{max}$ | 0.91 ± 0.27 (h) | 1.13 ± 0.23 (h) |

AUC: area under the plasma concentration time curves (mean values ± standard deviations)
$C_{max}$: maximum plasma concentrations
$t_{max}$: times necessary to reach the maximum plasma concentrations Table 4 and Graph I show the comparability of the biovailability of dispersible cimetidine tablets and of the commercial preparation, wherein in the former the values are somewhat higher and the maximum plasma concentration is reached faster.

Stability of Dispersible Tablets

The stability of dispersible tablets containing 400 mg of cimetidine together with sodium lauryl sulphate as surfactant, which were kept in brown glass vials, was determined on the basis of 12-month accelerated stability testing in the temperature range from 4° to 50° C.

The colour of the tablets was determined by naked eye, the cimetidine content was determined spectrophotometrically, related matter an disintegration products were determined by means of semiquantitative thin layer chromatography, the disintegrability and dispersibility were determined by gentle stirring in water at 20° C. The results are given in Table 5.

TABLE 5

| Tested parameter | time of keeping | conditions of keeping | | | | |
|---|---|---|---|---|---|---|
| | | 4 ± 1° C. | 20 ± 5° C. | 30 ± 1° C. | 40 ± 1° C. | 50 ± 1° C. |
| colour of tablets | 0 months | white | white | | | |
| | 3 months | white | white | white | almost white | almost white |
| | 6 months | white | white | white | almost white | almost white |
| | 12 months | white | white | almost white | almost white | slightly yellowish |
| cimetidine content | 0 months | | 99.5% | | | |
| | 3 months | 101.2% | — | — | 100.7% | 101.1% |
| | 6 months | 99.8% | 99.7% | 100.1% | 99.3% | 100.1% |
| | 12 months | 101.0% | 100.5% | 100.0% | 100.9% | 99.5% |
| related matter and disintegration products | 0 months | | 0.15% | | | |
| | 3 months | 0.15% | — | — | 0.15% | 0.15% |
| | 6 months | 0.15% | 0.15% | 0.15% | 0.2% | 0.2% |
| | 12 months | 0.2% | 0.2% | 0.2% | 0.2% | 0.2% |

Disintegrability and Dispersibility

| Time of keeping at 20 ± 5° C. | disintegrability and dispersibility |
|---|---|
| 0 months | within less than 1 min |
| 3 months | within less than 1 min |
| 6 months | within less than 1 min |
| 12 months | within less than 1 min |

The results show that after 12 months of accelerated testing the dispersible tablets remained practically unchanged with respect to the tested parameters. A 5-year stability can be foreseen, which is tantamount to the stability of the commercial preparation at about room temperature.

We claim:
1. Dispersible cimetidine tablets containing one of the polymorphous modifications of cimetidine A, B or C, comprising from 30 to 90% by weight of cimetidine, from 5 to 55% by weight of one or more disintegrating agents selected from the group consisting of starch, modified starches, microcrystalline cellulose, and cross-linked carboxymethyl cellulose, from 0.05 to 5.0% by weight of a surfactant selected from the group consisting of sodium lauryl sulphate, a polyoxyethylene-polyoxypropylene polymer of the formula

$$HO(CH_2CH_2O)_a-(CH(CH_3)CH_2O)_b(CH_2CH_2O)_cH,$$

wherein a is 75, b is 30, and c is 75, polyalkoxyalkylene sterol ethers of the formula $$RO(CH_2)_n-O_xH$$

wherein RO denotes the sterol moiety, n is an integer of 2 or 3 and x represents a number between 8 and 30; and wherein said cimetidine is employed in the form of particles the size of which particles is less than 200 μm with 95% of particles having a size of between 20 and 100 μm.

2. The tablets of claim 1 wherein said sterol moiety is selected from the group of lanosterol, dihydrocholesterol or cholesterol radical.

3. The dispersible tablets of claim 1 that contain at least two disintegrating agents.

4. The dispersible tablets of claim 1 wherein they amount of surfactant is 0.1 to 0.2% by weight.

5. The dispersible tablets of claim 1 wherein said surfactant is sodium lauryl sulphate.

6. The dispersible tablets of claim 1 wherein the content of cimetidine in the tablet is 200-800 mg.

7. The dispersible tablets of claim 1 wherein the content of cimetidine is 400 mg.

8. The dispersible tablets of claim 1 wherein the content of cimetidine is 800 mg.

9. The dispersible tablets of claim 1 wherein the amount of cimetidine is about 50%.

10. The dispersible tablets of claim 1 wherein the amount of disintegrating agents is about 32%.

11. The dispersible tablets of claim 1 which further comprise at least one common pharmaceutical adjuvant selected from the group consisting of binders, lubricating agents, fillers and flavoring, and taste-improving substances.

12. A process for the manufacture of dispersible cimetidine tablets containing one of the polymorphous modifications of cimetidine A, B or C comprising granulating a composition comprising 30 to 90% by weight of cimetidine, 5 to 55% by weight of one or more disintegrating agents selected from the group consisting of starch, modified starches, microcrystalline cellulose and cross-linked carboxymethyl cellulose; 0.05 to 5.0% by weight of a surfactant selected from the group consisting of sodium lauryl sulphate, a polyoxyethylene-polyoxypropylene polymer of the formula $$HO(CH_2CH_2O)_a-(CH(CH_3)CH_2O)_b(CH_2CH_2O)_cH,$$

wherein a is 75, b is 30 and c is 75, polyalkoxyalkylene sterol ethers of the formula $$RO(CH_2)_n\text{-}O_xH$$

wherein RO denotes the sterol moiety, n is an integer of 2 or 3 and x represents a number 8 and 30; and wherein said cimetidine is employed in the form of particles the size of which particles is less than 200 μm with 95% of particles having a size of between 20 and 100 μm; to provide a granulate, and compressing the granulate to tablets.

13. The process of claim 12 wherein said composition further comprises at least one common pharmaceutical adjuvant selected from the group consisting of binders, lubricating agents, fillers and flavoring, and taste-improving substances.

* * * * *